(12) United States Patent

Inagaki et al.

(10) Patent No.: US 7,943,110 B2
(45) Date of Patent: May 17, 2011

(54) CROSSLINKED CARBON NANOTUBE

(75) Inventors: Yoshio Inagaki, Ashigarakami-gun (JP);
Kenta Yoshida, Haibara-gun (JP);
Hirotaka Kitagawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 222 days.

(21) Appl. No.: 12/239,497

(22) Filed: Sep. 26, 2008

(65) Prior Publication Data

US 2009/0088582 A1  Apr. 2, 2009

(30) Foreign Application Priority Data

Sep. 27, 2007  (JP) ................. 2007-252721

(51) Int. Cl.
*D01F 9/12* (2006.01)
(52) U.S. Cl. .................... 423/447.2; 977/750; 556/143; 568/28; 423/445 B
(58) Field of Classification Search ............... 423/447.2, 423/445 B; 556/143; 568/28; 977/750, 977/752
See application file for complete search history.

(56) References Cited

U.S. PATENT DOCUMENTS 7,129,003 B2 * 10/2006 Cagle ..................... 429/231.8
2007/0161515 A1 * 7/2007 Bicerano ..................... 507/117

FOREIGN PATENT DOCUMENTS

JP  2002-503204 A  1/2002
WO  97/32571 A1  9/1997

OTHER PUBLICATIONS

Chen, J.; Cuihua, X., "A New Method for the Preparation of Stable carbon nanotube organogels.", Carbon 44 (2006) 214-2146.*
Tasis, D. "Chemistry of Carbon Nanotubes", Chem. Rev. 2006, 106, 1105-1136.*
Alan M. Cassell, et al; "Directed Growth of Free-StandingSingle-Walled Carbon Nanotubes"; J. Am. Chem. Soc. 1999, vol. 121, No. 34; pp. 7975-7976.

* cited by examiner

*Primary Examiner* — Stuart Hendrickson
*Assistant Examiner* — Richard M Rump
(74) *Attorney, Agent, or Firm* — Sughrue Mion, PLLC

(57) ABSTRACT

A crosslinked carbon nanotube, in which multiple carbon nanotubes therein are crosslinked with each other at multiple cross-linking sites via a connecting group containing a π-electron conjugation system, and the bond between the connecting group and the carbon nanotube is not an ester or amido bond.

10 Claims, No Drawings

CROSSLINKED CARBON NANOTUBE

FIELD OF THE INVENTION

The present invention relates to a crosslinked carbon nanotube.

BACKGROUND OF THE INVENTION

Carbon nanotubes (CNTs), with their unique shapes and characteristics, may find various applications. A carbon nanotube has a tubular shape of one-dimensional nature which is obtained by rolling one or more graphene sheets composed of six-membered rings of carbon atoms into a tube. A carbon nanotube formed from one graphene sheet is called a single-wall carbon nanotube (SWNT) while a carbon nanotube formed from multiple graphene sheets is called a multi-wall carbon nanotube (MWNT). SWNTs are about 1 nm in diameter whereas multi-wall carbon nanotubes are several tens nm in diameter, and both are far thinner than their predecessors, which are called carbon fibers.

One of the characteristics of carbon nanotubes resides in that the aspect ratio of length to diameter is very large since the length of carbon nanotubes is on the order of micrometers. Carbon nanotubes are unique in their extremely rare nature of being both metallic and semiconductive depending on the spiral structures because six-membered rings of carbon atoms in carbon nanotubes are arranged into a spiral. Normally, they are obtained as a mixture of metallic and semiconductive carbon nanotubes. In addition, the electrical conductivity of carbon nanotubes is very high and allows a current flow at a current density of 100 $MA/cm^2$ or more.

Carbon nanotubes excel not only in electrical characteristics but also in mechanical characteristics. That is, the carbon nanotubes are distinctively tough, as attested by their Young's moduli exceeding 1 TPa, which belies their extreme lightness resulting from being formed solely of carbon atoms. In addition, the carbon nanotubes have high elasticity and resiliency resulting from their cage structure. Having such various and excellent characteristics, carbon nanotubes are very appealing as industrial materials.

Applied researches that exploit the excellent characteristics of carbon nanotubes have been heretofore made extensively. To give a few examples, a carbon nanotube is added as a resin reinforcer or as a conductive composite material while another research uses a carbon nanotube as a probe of a scanning probe microscope. Carbon nanotubes have also been used as minute electron sources, electric field emission electron devices, and flat displays. An application that is being developed is to use a carbon nanotube as hydrogen storage.

As described above, carbon nanotubes are expected to find use in various applications, and their application as electronic materials and electronic devices has been attracting attention. Electronic devices such as a diode and a transistor have already been prototyped by using carbon nanotubes, and are expected to replace the existing silicon semiconductors.

However, it is extremely difficult to actually wire carbon nanotubes. At present, several techniques of wiring carbon nanotubes have been attempted.

A first technique includes: picking up one or several carbon nanotubes by using a manipulator in a scanning electron microscope; and arranging the one or several carbon nanotubes at a desired position. A technique for arranging carbon nanotubes by using a probe microscope may be given as an example of a modification of the first technique. However, the technique requires much time and labor. Therefore, the technique is suitable for fundamental studies but is not practical.

A second technique is a technique for orienting a carbon nanotube in a certain direction by using electrophoresis. With this technique, carbon nanotubes may be wired in one direction, but it is difficult to wire carbon nanotubes in plural directions. Thus, this technique is not realistic.

A third technique is a technique employing a chemical vapor deposition (CVD) method. The CVD method includes: using an acetylene gas or methane gas containing carbon as a raw material; and producing a carbon nanotube by a chemical decomposition reaction of the raw material gas.

A. Cassell, N. Franklin, T. Tombler, E. Chan, J. Han, and H. Dai, J. Am. Chem. Soc. 121, 7975-7976 (1999) discloses a method of wiring a carbon nanotube horizontally to a substrate. That is, disclosed is a technique including: fabricating a Si pillar on a substrate; mounting an additive on the top part of the pillar; and allowing a methane gas to flow to bridge a carbon nanotube between the pillars. The method by this technique has certainly enabled horizontal wiring. However, the probability of cross-linking is extremely low, and wiring at an arbitrary position is still difficult.

As described above, a technique for wiring one or several carbon nanotubes is still at a developmental stage.

In the meantime, a method for wiring or patterning using a carbon nanotube as a film has been developed. For example, pattern formation of a carbon nanotube has been heretofore performed by using a screen printing method or a photolithography technique. Each of those techniques is excellent in forming a pattern in a wide area at once, and is used for patterning of an electron source in a field emission type display (FED). However, in each of those methods, a carbon nanotube is merely dispersed in a solvent before application, or is mixed with a binder before application. Therefore, the carbon nanotube is insufficient in terms of performance such as a mechanical strength or electrical conductivity, and is hardly used directly as an electrode or an electric circuit.

JP-T-2002-503204 ("JP-T" means searched and published International patent application) discloses that a carbon nanotube with a three-dimensional structure can be formed by using a functionalized carbon nanotube. However, this publication merely discloses, a use of carbon nanotubes which are deposited onto a metal mesh followed by being made porous, for simple use as a chromatography-flow cell electrode. In this case, the carbon nanotube is porous and a functional group is bonded thereto in order to separate and absorb a passing substance. The publication also discloses carbon nanotubes bonded to each other by using an alkoxide of aluminum or silica (the alkoxide itself serves as an insulator) as a cross-linking agent.

However, because the alkoxide crosslinks with itself, the carbon nanotube structure obtained has polymeric alkoxide residues having a cross-linking degree of several dozens randomly forming chains, causing fluctuation of the distance between carbon nanotubes and the chemical structure at the cross-linking sites and consequently prohibiting production of carbon nanotube with intended properties, which in turn imposes various restrictions in use. In addition, the network structure of carbon nanotube formed is not sufficiently dense, and thus, such a carbon nanotube had a problem that it was difficult to use the favorable properties inherent to carbon nanotube such as favorable electrical and thermal conductivity and mechanical strength efficiently.

SUMMARY OF THE INVENTION

The present invention resides in a crosslinked carbon nanotube, wherein multiple carbon nanotubes therein are crosslinked with each other at multiple cross-linking sites via a connecting group containing a π-electron conjugation system, and the bond between the connecting group and the carbon nanotube is not an ester or amido bond.

Other and further features and advantages of the invention will appear more fully from the following description.

DETAILED DESCRIPTION OF THE INVENTION

The present invention provides the following means:

[1] A crosslinked carbon nanotube, wherein multiple carbon nanotubes therein are crosslinked with each other at multiple cross-linking sites via a connecting group containing a π-electron conjugation system, and the bond between the connecting group and the carbon nanotube is not an ester or amido bond.

[2] The crosslinked carbon nanotube described in the above item [1], wherein the π-electron conjugation system comprises at least one group selected from carbon-carbon double bond, carbon-nitrogen double bond, carbon-carbon triple bond, and heteroatoms having an unshared electron pair.

[3] The crosslinked carbon nanotube described in the above item [1] or [2], wherein the π-electron conjugation system comprises a combination of at least two groups selected from carbon-carbon double bond, carbon-nitrogen double bond, carbon-carbon triple bond, and heteroatoms having an unshared electron pair.

[4] The crosslinked carbon nanotube described in any one of the above items [1] to [3], wherein the π-electron conjugation system comprises a combination of at least two groups selected from benzene ring, carbon-carbon double bond, and carbon-carbon triple bond.

[5] The crosslinked carbon nanotube described in any one of the above items [1] to [4], wherein the connecting group binds to the carbon nanotube via a phenylene or vinylene group.

[6] The crosslinked carbon nanotube described in any one of the above items [1] to [4], wherein the connecting group binds to the carbon nanotube via a -G-$CH_2CH_2SO_2$— group, where G represents a bivalent group binding to the carbon nanotube.

[7] The crosslinked carbon nanotube described in any one of the above items [1] to [4], wherein the connecting group is a group represented by -M-$C_5H_4$-L-$C_5H_4$-M-, where M represents a transition metal atom, and L represents a bivalent group.

Hereinafter, the present invention will be described in detail.

The crosslinked carbon nanotube (hereinafter sometimes also referred to as "cross-linked carbon nanotube structure") according to the present invention is characterized in that multiple carbon nanotubes therein are bound to each other at multiple cross-linking sites via a connecting group containing a π-electron conjugation system (wherein, the bond between the connecting group and the carbon nanotube is not an ester or amido bond). The π-electron conjugation system is an electron system formed by neighboring sp2-hybridized or sp-hybridized atoms, which has a π-bond chain formed by the p orbitals, which extend in the direction perpendicular to the interatomic bond axis, aligned in the interatomic bond axial direction. The π-electron conjugation system preferably comprises at least one group selected from carbon-carbon double bond, carbon-nitrogen double bond, carbon-carbon triple bond, and heteroatoms having an unshared electron pair (also referred to as "a noncovalent electron pair" or "a nonbonding electron pair"); more preferable is a system comprising at least two groups selected from carbon-carbon double bond, carbon-nitrogen double bond, carbon-carbon triple bond, and heteroatoms having an unshared electron pair; and still more preferable is a system comprising at least two groups selected from of benzene ring, carbon-carbon double bond, and carbon-carbon triple bond.

Carbon nanotubes, which are the main component in the present invention, may be single-wall carbon nanotubes or multi-wall carbon nanotubes having two or more layers. Whether one or both types of carbon nanotubes are used (and, if only one type is to be used, which type is chosen) is selected appropriately taking into consideration the application of the composite or the cost.

Carbon nanotubes in the present invention include ones that are not exactly shaped like a tube, such as: a carbon nanohorn (a horn-shaped carbon nanotube whose diameter continuously increases from one end toward the other end) which is a variant of a single-wall carbon nanotube; a carbon nanocoil (a coil-shaped carbon nanotube forming a spiral when viewed in entirety); a carbon nanobead (a spherical bead made of amorphous carbon or the like with its center pierced by a tube); a cup-stacked nanotube; and a carbon nanotube with its circumference covered with a carbon nanohorn or amorphous carbon.

Furthermore, carbon nanotubes in the present invention may be ones that contain some substances inside, such as: a metal-containing nanotube which is a carbon nanotube containing metal or the like; and a peapod nanotube which is a carbon nanotube containing a fullerene or a metal-containing fullerene.

As described above, in the present invention, it is possible to employ carbon nanotubes of any mode, including common carbon nanotubes, variants of common carbon nanotubes, and carbon nanotubes with various modifications, without a problem in terms of reactivity. Therefore, the concept of "carbon nanotube" in the present invention encompasses all of the above.

Those carbon nanotubes are conventionally synthesized by a known method, such as arc discharge, laser ablation, and CVD method, and the present invention can employ any of the methods. However, arc discharge method in a magnetic field is preferable from the viewpoint of synthesizing a highly pure carbon nanotube.

The diameter of a carbon nanotube used in the present invention is preferably 0.3 nm or more and 100 nm or less. A diameter of the carbon nanotube exceeding this upper limit undesirably results in difficult and costly synthesis. A more preferable upper limit of the diameter of a carbon nanotube is 30 nm or less.

In general, the lower limit of the carbon nanotube diameter is about 0.3 nm from a structural standpoint. However, too small a diameter could undesirably lower the synthesis yield. It is therefore preferable to set the lower limit of the carbon nanotube diameter to 1 nm or more, more preferably 10 nm or more.

The length of a carbon nanotube used in the present invention is preferably 0.1 μm or more and 100 μm or less. A length of the carbon nanotube exceeding this upper limit undesirably results in difficult synthesis or requires a special synthesis method raising cost. On the other hand, a length of the carbon nanotube falling short of this lower limit undesirably reduces the number of cross-link bonding points per carbon nanotube. A more preferable upper limit of the carbon nanotube length is 10 μm or less, and a more preferable lower limit of the carbon nanotube length is 1 μm or more.

The carbon nanotube for use in the present invention may have a functional group reactive with cross-linking agent that is introduced for improvement in cross-linking efficiency.

In the present invention, carbon nanotubes can have any functional groups to be connected thereto without particular limitations, as long as functional groups selected can be added to the carbon nanotubes chemically and can prompt a cross-linking reaction with any type of cross-linking agent. Specific examples of such functional groups include —COOR, —COX, —MgX, —X (where X represents halogen), —OR, —$C_6H_4$OH, —$NR^1R^2$, —NCO, —NCS, —COOH, —OH, —$NH_2$, —SH, —$SO_3H$, —R'CHOH, —CHO, —CN, —COSH, —SR, —$SiR'_3$ (In the above formulae, R, $R^1$, $R^2$, and R' each independently represent a substituted or unsubstituted hydrocarbon group). Note that the functional groups are not limited to those examples.

Of these, it is preferable to select at least one functional group from the group comprising of —OH, —COOH, —COOR (where R represents a substituted or unsubstituted hydrocarbon group), —COX (where X represents a halogen atom), —$C_6H_4$OH, —$NH_2$, and —NCO. In that case, a cross-linking agent, which can prompt a cross-linking reaction with the selected functional group, is selected as the cross-linking agent.

Examples of treating methods to introduce functional groups into carbon nanotubes will be shown.

Hydroxyl groups or carboxyl groups can be introduced into carbon nanotubes by mixing carbon nanotubes with concentrated nitric acid and stirring the resultant mixture under heating. Phenyl groups having functional groups can be introduced into carbon nanotubes by mixing carbon nanotubes with benzenediazonium salts having functional groups in appropriate solvents such as water or acetic acid. Various functional groups can be introduced into carbon nanotubes by generating carbenes, nitrenes or benzynes having functional groups in the presence of carbon nanotubes.

The amount of functional groups to be introduced cannot be determined uniquely because the amount varies depending on the length and thickness of a carbon nanotube, whether the carbon nanotube is of a single-wall type or a multi-wall type, the type of a functional group, the intended purposes of the cross-linked carbon nanotube structure, etc. From the viewpoint of the strength of the cross-linked substance obtained, the amount of functional groups to be introduced is preferably the amount which can add two or more functional groups to each carbon nanotube.

The bond between the carbon nanotube and the connecting group containing a π-electron conjugation system in the crosslinked carbon nanotube structure according to the present invention is not an ester or amido bond.

The connecting group containing a π-electron conjugation system in the crosslinked carbon nanotube according to the present invention is preferably a group binding to the carbon nanotube via a phenylene or vinylene group. A group binding to the carbon nanotube via a -G-$CH_2CH_2SO_2$— group (wherein, G represents a bivalent group binding to the carbon nanotube, preferably, —O—, —NH—, —$CH_2$O—, or —S—) is also favorable.

Alternatively, the connecting group containing a π-electron conjugation system in the crosslinked carbon nanotube according to the present invention is preferably a group represented by -M-$C_5H_4$-L-$C_5H_4$-M- (wherein, M represents a transition metal atom, and L represents a bivalent group, preferably, —$(CH=CH)_n$—, —$(C_6H_4)_n$—, or the combination thereof).

The crosslinked carbon nanotube according to the present invention can be produced in reaction of carbon nanotube with a cross-linking agent.

Favorable examples of the cross-linking agents include vinylsulfone-based cross-linking agents and bismetallocene-based cross-linking agents.

Typical examples of the vinylsulfone-based cross-linking agents include VS-1: $CH_2$=CH—$SO_2$—$C_6H_4$—$SO_2$—CH=$CH_2$, VS-2: $CH_2$=CH—$SO_2$—$C_6F_4$—$SO_2$—CH=$CH_2$, VS-3: $CH_2$=CH—$SO_2$—$CH_2CH_2CH_2$—$SO_2$—CH=$CH_2$, VS-4: $CH_2$=CH—$SO_2$—$CH_2CH_2OCH_2$—$SO_2$—CH=$CH_2$ and the like. These compounds can be prepared, for example, according to the description in Nambara, "Chemical Pharmaceutical Bulletin", vol. 75, 1560-1563 (1956) and Amosova. S. V., "Russ. Chem. Bull.", 45(2), 414-416 (1996).

Typical examples of the bismetallocene-based cross-linking agents include FE-1: ferrocene-ferrocene, FE-2: ferrocene-P(=O)N$(C_2H_5)_2$-ferrocene, FE-3: ferrocene-C(=O)—C$(CH_3)_2$—C(=O)-ferrocene, FE-4: ferrocene-C(=O)—$CH_2CH_2$—C(=O)-ferrocene, FE-5: ferrocene-CH=CH—CH=CH—CH=CH-ferrocene, and the like.

The crosslinked carbon nanotube according to the present invention can be prepared, for example, in the following manner:

PREPARATIVE EXAMPLE 1

Carbon nanotube (CNT) is allowed to react with para-hydroxybenzenediazonium (see Woo-Jae Khim et al., Chem. Mater., 19, 1571-1576 (2007)), to give CNT-$C_6H_4$—OH.

A vinylsulfone-based cross-linking agent $CH_2$=CH—$SO_2$—$C_6H_4$—$SO_2$—CH=$CH_2$ is allowed to react with it, to give a crosslinked CNT, CNT-$C_6H_4$—O—$CH_2CH_2SO_2$—$C_6H_4$—$SO_2$—$CH_2CH_2$—O—$C_6H_4$—CNT.

PREPARATIVE EXAMPLE 2

Carbon nanotube (CNT) is allowed to react with a bismetallocene-based cross-linking agent ferrocene-CH=CH—CH=CH—CH=CH-ferrocene, to give a crosslinked CNT structure, CNT-Fe—$C_5H_4$—CH=CH—CH=CH—CH=CH—$C_5H_4$—Fe—CNT.

Electrical conduction between CNTs is based on hopping conduction in conventional crosslinked carbon nanotube structures, but in contrast in the crosslinked carbon nanotube according to the present invention, electron transfer between carbon nanotubes, which are connected to each other via π-electron conjugation system, thus allowing supply or withdrawal of electrons more easily than sigma bond, proceeds more efficiently, and thus, the crosslinked carbon nanotube according to the present invention is useful as a carbon material superior in electrical conductivity.

In addition, the conductive film thereof, which also has a property to reflect electromagnetic wave, can also be used as a λ/4-type electromagnetic wave absorbent. When used, the crosslinked carbon nanotube according to the present invention forms micro circuits of carbon nanotubes on a substrate, absorbing electromagnetic wave by conductive loss.

Conventional electromagnetic wave absorbents absorbed electromagnetic wave by magnetic loss of a ferromagnetic material such as ferrite, but the magnetic loss caused a problem that increase in the frequency of the electromagnetic wave to the gigacycle band or higher often resulted in insufficient polarization of magnetic pole and thus deterioration in electromagnetic wave-absorbing efficiency. Alternatively, electromagnetic wave-absorbing materials prepared by kneading a conventional carbon material in resin, wherein the carbon material is dispersed in the binder resin and the electromagnetic wave is absorbed by dielectric loss by a condenser formed by the dispersed carbon materials, had a problem that the binder impaired the electrical and thermal conductivities. In contrast, the crosslinked carbon nanotube according to the present invention can absorb electromagnetic wave efficiently without deterioration in electrical and thermal conductivities.

In addition, the crosslinked carbon nanotube according to the present invention, which is superior in electromagnetic wave-absorbing efficiency, can generate heat with the adsorbed electromagnetic wave. By using the principle above, it can also be used as an electromagnetic wave-visualizing sensor of detecting an electromagnetic wave by generating heat locally only in the region absorbing electromagnetic wave and identifying the heat generated. In this way, it is possible to visualize and detect the electromagnetic wave leaked from electromagnetic wave-generating devices such as microwave oven. Such an electromagnetic wave-visualizing sensor can be formed, for example, by coating a heat generating-visualizing microcapsule, such as that used in heat sensitive paper, as a colorant on a structure containing the crosslinked carbon nanotube according to the present invention, and the electromagnetic wave-irradiated region is visualized, based on the difference in color of the electromagnetic wave-absorbed region. For example, a colorant that changes its color according to temperature, such as cholesteric liquid crystal, may be coated as the colorant, replacing the heat-sensitive microcapsule above.

The crosslinked carbon nanotube according to the present invention can be used appropriately in various applications such as composite materials, hydrogen occlusion materials, gas occlusion materials, electronic materials (such as light-emitting material, optical material, electrode material, electromagnetic wave-absorbing material, semiconductor material, vibration damping material, vibration material, and abrasive material), electronic device materials (such as probe, sensor, illumination, transistor, capacitor, condenser, conductive material, and surge suppressor), pharmaceutical materials, bio materials, catalysts, lubricants, and other chemicals.

The present invention provides a new crosslinked carbon nanotube structure superior in electrical conductivity, thermal conductivity and mechanical strength.

The crosslinked carbon nanotube according to the present invention contains carbon nanotubes crosslinked with each other via a connecting group having a π-electron conjugation system, and thus, the electron transfer between the connected carbon nanotubes proceeds efficiently, making it superior in electrical conductivity. The crosslinked carbon nanotube structure is also superior in thermal conductivity and mechanical strength, because a three dimensional network structure is formed by cross-linking.

The present invention will be described in more detail based on the following examples, but the present invention is not limited thereto.

EXAMPLES

Example 1

(Crosslinked Multi-wall Carbon Nanotube Structure)

Cyclohexane (200 mL) and a multi-wall carbon nanotube (0.5 g) available from Wako Pure Chemical Industries are mixed and agitated at room temperature for 10 minutes. A bisferrocene compound FE-5 (15.8 g, 40 mmol), aluminum chloride 13.3 g, 100 mmol) and aluminum powder (0.68 g, 25 mmol) are added thereto, and the mixture is heated under reflux and under nitrogen for 8 hours. The mixture is cooled to 0° C. and added with methanol; the resulting solid is centrifuged; the sediment is washed in an ultrasonic bath with methanol, acetone, and then ether and then dried under reduced pressure at 60° C., to give a crosslinked multi-wall carbon nanotube. A small amount of ethanol is added thereto; the mixture is ultrasonicated into a suspension; a drop of the suspension is placed on a $SiO_2$/Si substrate; and the electrical conductivity of the spot after drying is determined to have a value higher than that obtained in Comparative Example 2.

Example 2

(Crosslinked Single-Wall Carbon Nanotube Structure)

A crosslinked single-wall carbon nanotube is prepared in a similar manner to Example 1, except that the multi-wall carbon nanotube is replaced with HiPco single-wall carbon nanotube. A small amount of ethanol is added thereto; the mixture is ultrasonicated into a suspension; a drop of the suspension is placed on a $SiO_2$/Si substrate; and the electrical conductivity of the spot after drying is determined to have a value higher than that obtained in Comparative Example 1.

Example 3

(Crosslinked Single-Wall Carbon Nanotube Structure)

HiPco single-wall carbon nanotube is added to 1% aqueous sodium dodecylsulfate solution; the mixture is ultrasonicated; and the precipitate is separated in an ultracentrifugal separator, to give a suspension of the single-wall carbon nanotube. The suspension is adjusted to a pH of 5.5 and 45° C.; and an aqueous solution of 4-hydroxybenzenediazonium tetrafluoroborate, which is prepared according to the method described in Woo-Jae Kim et al., Chemistry of Materials, vol. 19, p. 1571-1576, American Chemical Society 2007, (0.3 mmol/L, 500 μL) is added at a rate of approximately 20 μL/h by using a syringe pump to 5 mL of the suspension, while the suspension is agitated. The suspension is adjusted to be alkaline by addition of aqueous sodium hydroxide solution; a methanol solution of vinylsulfone compound VS-1 is added thereto; and the mixture is agitated at room temperature for 24 hours. The solvent is distilled off under reduced pressure; the residue is washed with water, methanol, and then acetone and dried under reduced pressure, to give a crosslinked single-wall carbon nanotube. A small amount of ethanol is added thereto; the mixture is ultrasonicated into a suspension; a drop of the suspension is placed on a $SiO_2$/Si substrate; and the electrical conductivity of the spot after drying is determined to have a value higher than that obtained in Comparative Example 1.

Comparative Example 1

(Preparation of the Crosslinked Multi-Wall Carbon Nanotube Structure Described in JP-A-2005-96055)

30 mg of multi-wall carbon nanotube powder (purity: 90%, average diameter: 30 nm, average length: 3 μm; product of Science Laboratory) was added to 20 mL of concentrated nitric acid (60 mass % aqueous solution, manufactured by Kanto Kagaku), and the mixture was heated under reflux at 120° C. for 20 hours, to give a carbon nanotube carboxylic acid.

The solution was allowed to cool to room temperature and then centrifuged under a condition of 5,000 rpm for 15 minutes, separating the supernatant liquid from the precipitate. The recovered precipitate was dispersed in 10 mL of purified water; the suspension was centrifuged again under a condition of 5,000 rpm for 15 minutes, separating the supernatant liquid from the precipitate (one washing operation). The washing operation was repeated five times, and finally, the precipitate was recovered.

30 mg of the carbon nanotube-carboxylic acid prepared in the step above was added to 25 mL of methanol (manufactured by Wako Pure Chemical Industries); 5 mL of concentrated sulfuric acid (98 mass %, product of Wako Pure Chemical Industries) was added thereto; and the mixture was heated under reflux at 65° C. for 4 hours, allowing methyl esterification.

After the solution was cooled to room temperature, it was filtered for separation of the precipitate. The precipitate was washed with water and recovered.

10 mg of the carbon nanotube carboxylic methyl ester thus obtained in the step above was added to 5 mL of glycerin (manufactured by Kanto Kagaku), and the mixture was mixed in an ultrasonic dispersing machine. Further, the mixture was added to 10 mL of a viscosity improver methanol.

The paint thus prepared was supplied dropwise on a $SiO_2$/Si substrate in an amount of approximately 0.1 mL by using a Pasteur pipette.

The substrate carrying the paint thus supplied was heated at 200° C. for 2 hours, allowing polymerization by ester-exchange reaction, to give a glycerin-crosslinked multi-wall carbon nanotube structure in the network structure. The electrical conductivity, as determined by two-terminal method, was approximately 10 S/cm.

Comparative Example 2

(Preparation of the Crosslinked Single-Wall Carbon Nanotube Structure Described in JP-A-2005-96055)

A glycerin-crosslinked single-wall carbon nanotube structure was prepared in a similar manner to Comparative Example 1, except that the multi-wall carbon nanotube powder used in Comparative Example 1 was replaced with 30 mg of a single-wall carbon nanotube powder (purity: 90%, average diameter: 1.2 nm, average length: 1.5 μm; product of Science Laboratory). The electrical conductivity, as determined by the two-terminal method, was approximately 20 S/cm.

Having described our invention as related to the present embodiments, it is our intention that the invention not be limited by any of the details of the description, unless otherwise specified, but rather be construed broadly within its spirit and scope as set out in the accompanying claims.

What we claim is:

1. A crosslinked carbon nanotube, wherein multiple carbon nanotubes therein are crosslinked with each other at multiple cross-linking sites via a connecting group containing a π-electron conjugation system, and the bond between the connecting group and the carbon nanotube is not an ester or amido bond, and wherein the connecting group covalently binds to the carbon nanotube via a -G-$CH_2CH_2SO_2$— group, where G represents a bivalent group binding to the carbon nanotube.

2. A crosslinked carbon nanotube, wherein multiple carbon nanotubes therein are crosslinked with each other at multiple cross-linking sites via a connecting group containing a π-electron conjugation system, and the bond between the connecting group and the carbon nanotube is not an ester or amido bond, and wherein the connecting group covalently binds to the carbon nanotube via a group represented by -M-$C_5H_4$-L-$C_5H_4$-M-, and M represents a transition metal atom, where L represents a bivalent group.

3. The crosslinked carbon nanotube according to claim 1, wherein G represents —$C_6H_4O$—.

4. The crosslinked carbon nanotube according to claim 1, wherein the π-electron conjugation system comprises at least one group selected from carbon-carbon double bond, carbon-nitrogen double bond, carbon-carbon triple bond, and heteroatoms having an unshared electron pair.

5. The crosslinked carbon nanotube according to claim 1, wherein the π-electron conjugation system comprises a combination of at least two groups selected from carbon-carbon double bond, carbon-nitrogen double bond, carbon-carbon triple bond, and heteroatoms having an unshared electron pair.

6. The crosslinked carbon nanotube according to claim 1, wherein the π-electron conjugation system comprises a combination of at least two groups selected from benzene ring, carbon-carbon double bond, and carbon-carbon triple bond.

7. The crosslinked carbon nanotube according to claim 2, wherein M represents Fe.

8. The crosslinked carbon nanotube according to claim 2, wherein the π-electron conjugation system comprises at least one group selected from carbon-carbon double bond, carbon-nitrogen double bond, carbon-carbon triple bond, and heteroatoms having an unshared electron pair.

9. The crosslinked carbon nanotube according to claim 2, wherein the π-electron conjugation system comprises a combination of at least two groups selected from carbon-carbon double bond, carbon-nitrogen double bond, carbon-carbon triple bond, and heteroatoms having an unshared electron pair.

10. The crosslinked carbon nanotube according to claim 2, wherein the π-electron conjugation system comprises a combination of at least two groups selected from benzene ring, carbon-carbon double bond, and carbon-carbon triple bond.

* * * * *